United States Patent
Svetlik et al.

(10) Patent No.: US 9,315,476 B2
(45) Date of Patent: Apr. 19, 2016

(54) ANTIVIRAL WATER-SOLUBLE PRODUCT WITH ANTI-HIV EFFECT, BASED ON IONIC SILVER AND METHYLENE BLUE COMPOUND; METHOD OF ITS PRODUCTION AND EXAMPLES OF HIV-INFECTED PATIENTS' TREATMENT

(71) Applicants: Harvey E. Svetlik, Grand Prairie, TX (US); Vasily Vasilievich Tretiakov, Novosibirsk (RU); Olga Vladimirovna Tretiakova, Novosibirsk (RU); Vladimir Nikolaevich Silnikov, Novosibirsk (RU); Vladimir Ivanovich Bouroumov, Novosibirsk (RU); Nikolai Gerasimovich Zhevachevsky, Novosibirsk (RU)

(72) Inventors: Harvey E. Svetlik, Grand Prairie, TX (US); Vasily Vasilievich Tretiakov, Novosibirsk (RU); Olga Vladimirovna Tretiakova, Novosibirsk (RU); Vladimir Nikolaevich Silnikov, Novosibirsk (RU); Vladimir Ivanovich Bouroumov, Novosibirsk (RU); Nikolai Gerasimovich Zhevachevsky, Novosibirsk (RU)

(*) Notice: Subject to any disclaimer, the term of this patent is extended or adjusted under 35 U.S.C. 154(b) by 0 days.

(21) Appl. No.: 14/680,577

(22) Filed: Apr. 7, 2015

(65) Prior Publication Data

US 2015/0291542 A1 Oct. 15, 2015

Related U.S. Application Data

(60) Provisional application No. 61/977,897, filed on Apr. 10, 2014.

(51) Int. Cl.
*C07D 279/20* (2006.01)

(52) U.S. Cl.
CPC .................................. *C07D 279/20* (2013.01)

(58) Field of Classification Search
CPC ....................................................... C07D 279/20
USPC ............................................................ 544/37
See application file for complete search history.

(56) References Cited

FOREIGN PATENT DOCUMENTS

| RU | 2390343 C1 | 5/2010 |
|---|---|---|
| WO | 2007061337 A1 | 5/2007 |

OTHER PUBLICATIONS

Hulser, Dieter F., Localization of Reductive Sites in Bacteria by Methylenblue-Silver (Argochrome) with the Electron Microscope; Article; 18 pages; Jul. 2, 1968.

*Primary Examiner* — Kahsay Habte
(74) *Attorney, Agent, or Firm* — Charles Gunter

(57) ABSTRACT

A new antiviral water-soluble pharmacological product with anti-HIV effect, is based on ionic silver and methylene blue compound. The new substance is produced in the form of water-soluble powder that can be used for the preparation of finished dosage forms for treating viral infections, especially HIV infection. The product has a potential ability to radically suppress the infectious agents without leading to any mutations and resistance of viruses. The composition of the new product proposed under the conventional name Argothiazin-A™ corresponds to the chemical formula: $C_{20}H_{24}AgN_3O_4S$.

1 Claim, No Drawings

ANTIVIRAL WATER-SOLUBLE PRODUCT WITH ANTI-HIV EFFECT, BASED ON IONIC SILVER AND METHYLENE BLUE COMPOUND; METHOD OF ITS PRODUCTION AND EXAMPLES OF HIV-INFECTED PATIENTS' TREATMENT

CROSS REFERENCE TO RELATED APPLICATIONS

The present application claims priority from a previously filed provisional application, Ser. No. 61/977,897, filed Apr. 10, 2014, entitled "Antiviral Water-Soluble Product with Anti-HIV Effect, Based On Ionic Silver and Methylene Blue Compound; Method Of Its Production and Examples Of HIV-infected Patients' Treatment", by the same inventors.

BACKGROUND OF THE INVENTION

1. Field of the Invention

This invention relates generally to the field of pharmaceutical chemistry and medical science and, more specifically, to a new antiviral water-soluble pharmacological product with anti-HIV effect, based on ionic silver and methylene blue compound, as well as its production method, and includes the examples of HIV-infected patient's treatment.

2. Description of the Prior Art

Far back in the past, there used to be a medicine based on the compound of methylene blue in nitrate form and silver nitrate; it was manufactured in Germany by Merck under the Argochrom trade name from 1916 to 1945 and was imported to a number of countries. The composition of Argochrom corresponds to the Patent of Austria No. 69476 (branded equivalent) valid since 1914; the name of the substance in German was "Silber methylene blau" until 1920.

Argochrom powder was distinguished by increased toxicity and flammability due to a high content of nitrate in molecule structure. This medicine was intended for treating bacterial infections such as gonorrhea, while its antiviral effect was unknown at that time.

According to the Claim of Patent of Austria No. 69476 for the Production Method, the silver and dye compound was produced in two stages, while we have developed a one-stage synthesis procedure for the new composition complex, namely by using an organic silver compound instead of highly water-soluble silver salt, such as silver nitrate which was used for the production of the Argochrom medicine.

Also, there is the Patent of Russia No. 2390343, date of priority Dec. 15, 2008 (prototype) titled "Water-soluble substance with antiviral and immunomodulatory effect, based on the ionic silver and methylene blue compound, as well as its production method."

Since silver chloride is water-insoluble, the method of target product synthesis described in this patent involved the use of aqueous ammonia in large amounts to produce a transient soluble unstable complex with ammonia, which makes the process environmentally harmful and may lead to explosion hazards in case of technology violations.

The advantage of the ammonia-based technology was no loss of silver (50% of the metal was in the form of silver chloride and thus, no need to compensate for such losses using the complicated technology of silver regeneration).

Compared to Argochrom being a branded equivalent of Argothiazin-A claimed herein, the dry product obtained according to the above mentioned Patent of Russia was not flammable.

It is common knowledge that ions of silver are active killers of various pathogenic bacteria and viruses.

Methylene blue is a phenothiazine dye. Dyes of this type are able to penetrate into the structure of nucleic acids of viruses and block virus reproduction inside the host cell by tight binding with nucleoside bases of viruses containing both DNA and RNA.

SUMMARY OF THE INVENTION

The present invention discloses a new antiviral water-soluble pharmacological product with anti-HIV effect, based on ionic silver and methylene blue compound, as well as its production method, and includes the examples of HIV-infected patients' treatment. The new substance which is produced in the form of water-soluble powder, can be used for the preparation of finished dosage forms for treating viral infections, especially HIV infection.

At the present time, to the best of Applicants' knowledge, there are no medicines based on the compound of ionic silver and organic components. Compared to the existing medicines for HIV treatment, the present products based on ionic silver and methylene blue compound have a potential ability to radically suppress the infectious agents without leading to any mutations and resistance of viruses. The composition of the new product disclosed herein is proposed under the conventional name Argothiazin-A™ and corresponds to the chemical formula: $C_{20}H_{24}AgN_3O_4S$.

The proposed method of the production of the new antiviral water-soluble product with anti-HIV effect, based on the ionic silver and methylene blue compound, consists in the synthesis under heating up to 90-95° C., by mixing the following ingredients: methylene blue and silver acetate in mole ratio 1:1.96; during this process, methylene blue is dissolved in water at 60-70° C., and then a preliminarily prepared solution of silver acetate is added at 80° C. The reaction is left for one hour, cooled down, silver chloride is filtered out, the solution is then evaporated in vacuum, the solid residue is mixed with acetone and stirred to obtain a homogenous substance, after which the deposit is filtered, washed with acetone, and dried to constant weight in vacuum at ambient temperature.

Additional objects, features and advantages will be apparent in the written description which follows.

DETAILED DESCRIPTION OF THE INVENTION

The preferred version of the invention presented in the following written description and the various features and advantageous details thereof are explained more fully with reference to the non-limiting examples included and as detailed in the description which follows. Descriptions of well-known components and processes and manufacturing techniques are omitted so as to not unnecessarily obscure the principal features of the invention as described herein. The examples used in the description which follows are intended merely to facilitate an understanding of ways in which the invention may be practiced and to further enable those skilled in the art to practice the invention. Accordingly, the examples should not be construed as limiting the scope of the claimed invention.

It is common knowledge that ions of silver are active killers of various pathogenic bacteria and viruses. Methylene blue is also a known compound and is a phenothiazine dye. Dyes of this type are able to penetrate into the structure of nucleic acids of viruses and block virus reproduction inside the host cell by tight binding with nucleoside bases of viruses containing both DNA and RNA.

The objective of the invention was to develop a non-toxic formula of the medical compound combining the pharmaceutical properties of methylene blue and ionic silver and to produce a medicine for HIV and other concurrent infections.

The combination of silver ions with methylene blue allows for the creation of a complex which, firstly, represents a stable molecular compound not decomposing in a human body and not releasing ions to the transport globulins in blood and, secondly, has a powerful synergetic effect, as its main ingredients methylene blue and silver ions enhance each other's curative action. The product obtained under the developed technology is water-soluble powder.

The novelty of this patent proposal consists in the idea itself and in the method of the production of the new ionic silver and methylene blue compound with antiviral effect, including anti-HIV activity; the new compound can be included in the list of highly efficient medicines for HIV patients' treatment.

The main advantage of the developed compound is that each of its ingredients has unique curative properties which are enhanced when combined. The produced substance is specific for its increased stability (i.e. it does not decompose in a human body for a considerable time); it easily penetrates into the infected cells and destroys HIV as well as nonviable cells affected by the virus.

It is possible to create efficient and non-toxic medicines based on the substance proposed herein for HIV-infected patient's treatment. At present, there are no medicines based on the compounds of ionic silver and organic components. Compared to the existing medicines for HIV treatment, the products based on the ionic silver and methylene blue compound have a potential ability to radically suppress the infectious agents without leading to any mutations and resistance of viruses.

The developed formula with the conventional name Argothiazin-A™ is a neutral complex of two organic acetate anions and one double-charged cation formed by the combination of silver ion and organic ion of methylene blue, which enables efficient penetration of the substance through various biological membranes starting from the penetration into blood stream in case of oral or rectal administration of the medicine to a patient's body, followed by further penetration to intercellular space, reaching the cells infected by virus and penetrating through cell membranes into the infected cells. There the medicine destroys DNA matrices of the virus, and affects the mitochondria of a host cell, thus stopping its vital activity, after which the host cell is removed from the body by the macrophage component of the human immune system.

The goals of the present invention are achieved by obtaining water-soluble, light-resistant preparation of silver represented by a stable metal complex of silver and methylene blue. While not wishing to be bound by any particular theory, it appears to Applicants that a main advantage of the claimed compound formula under the conventional name Argothiazin-A™ is that non-organic anions are fully excluded from the ionic silver and methylene blue complex by replacing them with organic acetate anions resistant to oxidization by ionic silver. This considerably enhances the transport of silver ions through biological membranes by fully protecting silver ions from transfer to sulfur-containing transport globulins in the blood. It also provides for the transport of the silver-containing complex with methylene blue into virus-infected cells and then the transmembrane transfer into pathologic cells where molecules of Argothiazin-A™, affected by reducing coenzyme NAD-H decompose, with methylene blue being transformed into hydrogen-reduced colorless leucoform. This leucoform reversibly transforms into an oxidized blue form under the influence of oxygen arriving to mitochondria during the aerobic phase of the oxidation cycle. These processes take place in the mitochondria of cells, which leads to the damage of cells infected by the virus up to their apoptosis. On the other hand, free ions of silver released during complex decomposition diffuse into both protein components and DNA or RNA structures of viruses, bind with them and effectively prevent their further association into an active virus.

Also, a novel method for the production of the new antiviral water-soluble medicine (substance) is proposed; it consists in the synthesis under heating up to 90-95° C., by mixing the following ingredients: methylene blue and silver acetate in mole ratio 1:1.96; during this process, methylene blue is dissolved in water at 60-70° C., and then a preliminarily prepared solution of silver acetate is added at 80° C.

The chemical composition of the proposed medicine is $C_{20}H_{24}AgN_3O_4S$, which corresponds to the following assumed structure:

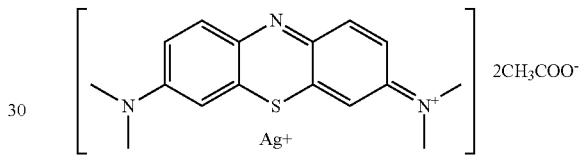

Example of Carrying Out the Method.

Methylene blue (16.3 g, 51 mmole) is dissolved in 200 mL of distilled water by thorough mixing under heating up to 60-70° C.; then a preliminarily prepared solution of silver acetate (16.7 g, 100 mmole) in 700 mL of distilled water is added at 80° C. The reaction is heated up to 90-95° C. while stirring and is left for one hour while stirring. The reaction is cooled down, the deposit is filtered out, and the resulting solution is evaporated in a rotary evaporator. Acetone in the amount of 0.5 L is added to the solid residue and is left in the magnetic mixer for three hours. The deposit is filtered out and washed with a few portions of acetone (total volume of acetone is 1.2 L). The deposit is dried on a filter and then in a vacuum desiccator until constant weight is reached. The weight of the final product is 21.9 g (86.0%).

The elemental analysis data of the claimed substance, obtained using the automatic element composition analyzer, are shown in Table 1. The content of silver is determined by the atomic adsorption method.

TABLE 1

| Elemental analysis data | | | | |
|---|---|---|---|---|
| C | H | N | S | Ag |
| Found (%) | | | | |
| 47.14 | 4.92 | 8.09 | 6.18 | 21.15 |
| 47.05 | 4.65 | 8.19 | 6.24 | 21.03 |
| 47.02 | 4.78 | 8.22 | 6.31 | 21.27 |
| Calculated (%) for $C_{20}H_{24}AgN_3O_4S$ | | | | |
| 47.07 | 4.74 | 8.23 | 6.28 | 21.14 |

Screening of Claimed Argothiazin-A in Terms of
Anti-HIV Activity In Vitro Assay of Argothiazin-A
Cytotoxicity Using Passaged Culture of Human
T-Lymphocytes (MT-4 Cell Line)

Serial 10-fold dilutions of the test compound stock solution were prepared using RPMI-1640 medium (from 1,000 μg/mL to 0.1 μg/mL), and 200 μL of corresponding dilutions were added to 10 the wells of 96-well plates (three wells per each dilution) for cells seeding. The seeding concentration of cells was $5 \cdot 10^5$ cells/mL. The final concentration of Argothiazin-A in the cell suspension was from 100 μg/mL to 0.01 μg/mL.

The cells had been incubated in Costar 96-well plates for cell cultures (USA) in the growth medium (RPMI-1640 medium with 10% of fetal bovine serum manufactured by ICN (USA), 0.06% of L-glutamine, 100 μg/mL of gentamycin, and 60 μg/mL of lincomycin) at 37° C. and 5% $CO_2$ for 4 days.

As soon as incubation was completed, the proportion of viable cells was counted in the Goryaev chamber after staining the culture with trypan blue.

The dose-rate curve was then plotted, and the concentration of claimed Argothiazin-A resulting in the death of 50% of cells ($CD_{50}$) was identified (see Table 2).

Assessment of Anti-HIV Activity of Claimed Argothiazin-A

MT-4 cells at a concentration of $2 \cdot 10^6$ cells/mL were infected with HIV-1/EVK strain with the multiplicity of infection being 0.2-0.5 of viral particles per cell, and incubated at 37° C. for one hour (virus adsorption). The suspension of infected cells was diluted with RPMI-1640 growth medium containing 10% of fetal bovine serum manufactured by ICN (USA), 0.06% of L-glutamine, 100 μg/mL of gentamycin, and 60 μg/mL of lincomycin, up to the seeding concentration of $5 \cdot 10^5$ cells/mL, and was added to the wells of a 96-well culture plate. Aliquots of serial dilutions of the study product Argothiazin-A were then added to the wells (three wells per each dilution). The final concentration of the study product Argothiazin-A™ in the cell suspension was from 100 μg/mL to 0.01 μg/mL.

The test cells (with the medicine) and control cells (without the medicine) infected with HIV-1 as well as non-infected control cells (without the medicine) had been incubated at 37° C. and 5% $CO_2$ for 4 days. As soon as incubation was completed, the proportion of viable cells was counted in the Goryaev chamber after staining the culture with a solution of trypan blue; also, the level of virus-specific protein p24 accumulation was controlled using the enzyme-linked immunoassay method.

Based on the experimental data, on the $4^{th}$ day of incubation, the inhibiting effect of the claimed Argothiazin-A™ was evaluated against the cytopathic effect of virus, by assessing the extent of infected cells protection from termination as a result of a viral infection. To do this, the proportion of viable cells was counted in the Goryaev chamber after staining the culture with trypan blue.

Based on the quantitative data obtained in the course of the experiment, a dose-rate curve was plotted to identify both the inhibiting dose $ID_{50}$ (μg/mL) against infected cells protection with the claimed Argothiazin-A™, and the inhibiting doze $ID_{50}$ (μg/mL) of Argothiazin-A™ against the accumulation of virus antigen p24 compared to control cells (MT-4 cells infected with HIV-1) (see Table 2).

Argothiazin-A™ showed the highest activity in the range of concentrations from 5 μg/mL to 15 μg/mL; this means that dosage over 15 μg/mL increases the cytotoxicity of Argothiazin-A™, while the dosage less than 5 μg/mL reduces its antiviral protective properties.

According to the Argochrom article from the reference book published in the Russian language, Вотчал Б.Е. и др. «Фармацевтические препараты». М.Л.:ОНТИ, 1934, с. 49, the medicinal product Argochrom (manufactured by Merck), the claimed Argothiazin-A™ analogue that used to be well-known in the past, was administered to people intravenously in a single dose of up to 0.2 g per 24 hours.

It is evident that the only difference between the molecular composition of these two medicines consists in a different composition of anions which provide a neutral charge to the molecules of these medicines; in particular, there were nitrate anions in the previously used Argochrom, while in Argothiazin-A™ claimed herein there are acetate anions which are natural for a human body as they are released from edible organic acetic acid, while nitrate anions are released from nitric acid that is toxic for humans.

The pharmacological advantages of such replacement in the composition of the claimed Argothiazin-A™ are described in the beginning of this invention disclosure and involve more complete protection of silver ions from human blood components, particularly from early decomposition of the ionic silver and methylene blue compound; moreover, the claimed Argothiazin-A™ is transported more efficiently through the membranes of cells infected with virus and penetrates through the protein coat of virus towards its DNA or RNA to block the process of HIV-1 replication and to terminate infected cells by blocking its vital enzymes and by the active effect of methylene blue on oxidization processes in the mitochondria of pathologic cells up to their apoptosis.

Examples of Outpatient Treatment of HIV-Infected
Volunteer Patients, Citizens of Russia, on the
Territory of Russia, Upon their Informed Consent Case 1

Patient K., 30 years old, subject to a regular medical check-up at one of the Russian Centers for AIDS Prevention and Treatment, diagnosis: HIV infection. The patient had not been referred for standard antiretroviral therapy at the Center. The clinical signs of the disease corresponded to stage 3 (according to the classification adopted in the Russian Federation) and represented a slight loss of weight (up to 10%), persistent generalized lymphadenopathy, and general weakness after moderate physical exercises and walking.

A course of treatment had been conducted with Argothiazin-A™ in the medicinal form of substance powder in gelatin capsules, by oral administration of 0.2 g of the claimed medicine substance before evening meal once a day for 10 days.

This patient had three courses of the antiviral therapy with the claimed Argothiazin-A™ as described above, with 20-day breaks between the courses. After the three courses of treatment, a PCR test revealed full absence of viral load in the patient's blood plasma (see Table 3.1 Virological parameters of patient K. during treatment). Six months after treatment completion, the level of viral load did not increase (Table 3.1), and the immunological parameters improved (see Table 4.1), which is indicative of the good long-term results of the antiviral therapy with the claimed Argothiazin-A™.

Case 2

Patient M., 35 years old, subject to regular medical check-up at one of the Russian Centers for AIDS Prevention and Treatment, diagnosis: HIV infection. The patient had not been referred for standard antiretroviral therapy at the Center. There were no clinical signs of the disease at the moment of treatment commencement; however, the Center diagnosed stage 3 of the disease (according to the classification adopted in the Russian Federation).

A course of treatment had been conducted with Argothiazin-A™ in the medicinal form of substance powder in gelatin capsules, by oral administration of 0.2 g of the claimed medicine substance before evening meal once a day for 10 days.

This patient had three courses of the antiviral therapy with the claimed Argothiazin-A™ as described above, with 20-day breaks between the courses. After the three courses of treatment, a PCR test revealed full absence of viral load in the patient's blood plasma (see Table 3.2 Virological parameters of patient M. during treatment). Six months after treatment completion, the level of viral load did not increase (Table 3.2), and the immunological parameters improved (see Table 4.2), which is indicative of the good long-term results of the antiviral therapy with the claimed Argothiazin-A™.

TABLE 2

| Product name | $CD_{50}$ µg/mL | $ID_{50}$ µg/mL Protection of HIV-1 infected cells | $ID_{50}$ µg/mL p24 accumulation inhibiting | IS Protection of HIV-1 infected cells | IS p24 accumulation inhibiting |
|---|---|---|---|---|---|
| Argothiazin-A ™ | 20 | 1 | 2 | 20 | 10 |

TABLE 3.1

Virological parameters of patient K. during treatment (Case 1)

| | Before treatment | After Course 1 | After Course 2 | After Course 3 | In 6 months | Norm |
|---|---|---|---|---|---|---|
| PCR (HIV-1 RNA) in 1 mL of blood serum | >10$^5$ | <10$^4$ | <10$^3$ | 0 | 0 | 0 |
| PCR (HIV-1 DNA, intracellular matrix) in T-lymphocytes in 1 mL of blood | >10$^2$ | <10$^2$ | 0 | 0 | 0 | 0 |

TABLE 3.2

Virological parameters of patient M. during treatment (Case 2)

| | Before treatment | After Course 1 | After Course 2 | After Course 3 | In 6 months | Norm |
|---|---|---|---|---|---|---|
| PCR (HIV-1 RNA) in 1 mL of blood serum | >3·10$^3$ | <5·10$^2$ | <10$^2$ | 0 | 0 | 0 |
| PCR (HIV-1 DNA, intracellular matrix) in T-lymphocytes in 1 mL of blood | <10$^2$ | 0 | 0 | 0 | 0 | 0 |

TABLE 4.1

Case 1 Immunological parameters of blood in patient K.

| | Before treatment | After Course 3 | In 6 months after treatment | Norm |
|---|---|---|---|---|
| Number of CD4 T-lymphocytes in 1 µL of blood serum | 321 | 412 | 600 | >500 |
| Number of CD8 T-lymphocytes in 1 µL of blood serum | 616 | 550 | 500 | >300 |
| IRI (immunoregulatory index (CD4/CD8)) | 0.52 | 0.75 | 1.2 | (0.9-2.8) |
| CIC (circulating immune complexes) | 92 | 49 | 23 | (3-23) |

TABLE 4.2

Case 2 Immunological parameters of blood in patient M.

| | Before treatment | After Course 3 | In 6 months after treatment | Norm |
|---|---|---|---|---|
| Number of CD4 T-lymphocytes in 1 µL of blood serum | 361 | 421 | 580 | >500 |
| Number of CD8 T-lymphocytes in 1 µL of blood serum | 586 | 510 | 530 | >300 |
| IRI (immunoregulatory index (CD4/CD8)) | 0.62 | 0.83 | 1.09 | (0.9-2.8) |
| C1C (circulating immune complexes) | 41 | 29 | 21 | (3-23) |

An invention has been provided with several advantages. A new antiviral water-soluble pharmacological product has been described with anti-HIV effect, based on the ionic silver and methylene blue compound. Also a production method has been described, and includes examples of HIV-infected patients' treatment. The invention can be used for the preparation of finished dosage forms for treating viral infections, and is especially efficient for HIV infection. The objective is to develop highly efficient antiviral medicines, especially for HIV-infection including cases complicated by mycotic infection and other mixed infections resistant to standard medical therapy.

What is claimed is:

1. A method for the production of the new antiviral water-soluble product with antiviral and anti-HIV effect, based on the ionic silver and methylene blue compound, the method comprising the steps of:
    the synthesis under heating up to 90-95° C., by mixing the following ingredients: methylene blue and silver acetate in mole ratio 1:1.96;
    during such synthesis, methylene blue is dissolved in water at 60-70° C., and then a preliminarily prepared solution of silver acetate is added at 80° C.;

the reaction is left for one hour and allowed to cool, silver chloride is filtered out, and the solution is then evaporated in vacuum, leaving a solid residue;

the solid residue is then mixed with acetone and stirred to obtain a homogenous substance which makes up a deposit;

after which the homogeneous substance making up the deposit is filtered, washed with acetone, and dried to constant weight in vacuum at ambient temperature; and wherein the water-soluble substance with antiviral and anti-HIV effect, based on ionic silver and methylene blue compound produced by the method as described in above and corresponding to the composition $C_{20}H_{24}AgN_3O_4S$, has the chemical structure as follows:

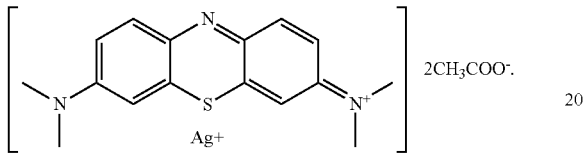

2CH$_3$COO$^-$.

* * * * *